US011986349B2

(12) United States Patent
Fife et al.

(10) Patent No.: US 11,986,349 B2
(45) Date of Patent: May 21, 2024

(54) ULTRASOUND DEVICES

(71) Applicant: BFLY OPERATIONS, INC., Guilford, CT (US)

(72) Inventors: Keith G. Fife, Palo Alto, CA (US); Jianwei Liu, Fremont, CA (US); Joseph Lutsky, Los Altos, CA (US); Sarp Satir, San Francisco, CA (US); Jungwook Yang, Newton, MA (US)

(73) Assignee: BFLY OPERATIONS, INC., Burlington, MA (US)

( * ) Notice: Subject to any disclaimer, the term of this patent is extended or adjusted under 35 U.S.C. 154(b) by 1012 days.

(21) Appl. No.: 16/401,630

(22) Filed: May 2, 2019

(65) Prior Publication Data

US 2019/0336104 A1   Nov. 7, 2019

Related U.S. Application Data

(60) Provisional application No. 62/666,643, filed on May 3, 2018.

(51) Int. Cl.
*A61B 8/00* (2006.01)
*A61B 8/06* (2006.01)
(Continued)

(52) U.S. Cl.
CPC .............. *A61B 8/4483* (2013.01); *A61B 8/06* (2013.01); *B06B 1/00* (2013.01); *B06B 1/0292* (2013.01);
(Continued)

(58) Field of Classification Search
CPC ....... A61B 8/4483; A61B 8/06; A61B 8/4444; A61B 8/483; A61B 8/5207; B06B 1/00; B06B 1/0292; B06B 2201/76
See application file for complete search history.

(56) References Cited

U.S. PATENT DOCUMENTS 6,430,109 B1   8/2002   Khuri-Yakub et al.
6,694,817 B2   2/2004   Degertekin et al.
(Continued)

FOREIGN PATENT DOCUMENTS

WO   WO 2019/152340 A1   8/2019
WO   WO 2019/173694 A1   9/2019

OTHER PUBLICATIONS

International Preliminary Report on Patentability dated Nov. 12, 2020 in connection with International Application No. PCT/US2019/030482.
(Continued)

*Primary Examiner* — Su C Kim
(74) *Attorney, Agent, or Firm* — Carter, DeLuca & Farrell LLP (57) ABSTRACT

An ultrasound device is described. The ultrasound device may include a cavity, a membrane, and a sensing electrode. When an electrical signal is applied to the sensing electrode and a static bias is applied to the membrane, the membrane vibrates within the cavity and produces ultrasonic signals. The cavity, the membrane, and the sensing electrode may be considered a capacitive micromachined ultrasonic transducer (CMUT). The sensing electrode may be shaped as a ring, whereby the central portion of the sensing electrode is removed. Removal of the central portion of the sensing electrode may reduce the parasitic capacitance without substantially affecting the production of ultrasonic signals by the CMUT. This, in turn, can result in an increase in the signal-to-noise ratio (SNR) of the ultrasonic signals. The ultrasound device may further include a bond pad configured for wire bonding, and a trench electrically isolating the bond pad from the membrane.

5 Claims, 9 Drawing Sheets

(51) Int. Cl.
  *B06B 1/00* (2006.01)
  *B06B 1/02* (2006.01)
  *A61B 8/08* (2006.01)

(52) U.S. Cl.
  CPC ............ *A61B 8/4444* (2013.01); *A61B 8/483* (2013.01); *A61B 8/5207* (2013.01); *B06B 2201/76* (2013.01)

(56) References Cited

U.S. PATENT DOCUMENTS

| | | |
|---|---|---|
| 6,779,387 B2 | 8/2004 | Degertekin |
| 6,958,255 B2 | 10/2005 | Khuri-Yakub et al. |
| 7,312,440 B2 | 12/2007 | Degertekin et al. |
| 7,441,447 B2 | 10/2008 | Degertekin et al. |
| 7,615,834 B2 | 11/2009 | Khuri-Yakub et al. |
| 7,846,102 B2 | 12/2010 | Kupnik et al. |
| 9,067,779 B1* | 6/2015 | Rothberg ............... B81B 7/007 |
| 9,132,693 B2 | 9/2015 | Klootwijk et al. |
| 9,505,030 B2 | 11/2016 | Rothberg et al. |
| 9,521,991 B2 | 12/2016 | Rothberg et al. |
| 9,592,030 B2 | 3/2017 | Rothberg et al. |
| 2007/0215964 A1 | 9/2007 | Khui-Yakub et al. |
| 2009/0122651 A1 | 5/2009 | Kupnik et al. |
| 2010/0202254 A1 | 8/2010 | Roest et al. |
| 2011/0055447 A1 | 3/2011 | Costa |
| 2013/0089224 A1* | 4/2013 | Dehe ................. H04R 7/04 381/191 |
| 2016/0282326 A1* | 9/2016 | Waduge ........... G01N 27/44791 |
| 2016/0379973 A1 | 12/2016 | Rothberg et al. |
| 2017/0021391 A1 | 1/2017 | Guedes et al. |
| 2017/0143306 A1 | 5/2017 | Rothberg et al. |
| 2017/0156696 A1* | 6/2017 | Takezaki ............... G01B 17/02 |
| 2017/0320091 A1* | 11/2017 | Budzelaar ............. B06B 1/0292 |
| 2018/0369862 A1 | 12/2018 | Alie et al. |
| 2019/0047850 A1 | 2/2019 | Rothberg et al. |
| 2019/0064021 A1* | 2/2019 | Kühne ................. G01L 9/0016 |
| 2019/0231312 A1 | 8/2019 | Fife et al. |
| 2019/0275561 A1 | 9/2019 | Fife et al. |

OTHER PUBLICATIONS

Daft et al., Microfabricated ultrasonic transducers monolithically integrated with high voltage electronics. Proc Ultrason Symp. 2004;493-6.

Gurun et al., Front-end CMOS electronics for monolithic integration with CMUT arrays: circuit design and initial experimental results. Proc Ultrason Symp. 2008;390-3.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Kupnik et al., CMUT Fabrication Based on a Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

Noble et al., A cost-effective and manufacturable route to the fabrication of high-density 2D micromachined ultrasonic transducer arrays and (CMOS) signal conditioning electronics on the same silicon substrate. Proc Ultrason Symp. 2001;941-5.

Noble et al., Low-temperature micromachined CMUTs with fully-integrated analogue front-end electronics. Proc Ultrason Symp. 2002;1045-50.

Zahorian et al., Single chip CMUT arrays with integrated CMOS electronics: fabrication process development and experimental results. Proc Ultrason Symp. 2008;386-9.

Zhuang et al., Wafer-bonded 2-D CMUT arrays incorporating through-wafer trench-isolated interconnects with a supporting frame. IEEE Trans Ultrason Ferroelectr Freq Control. Jan. 2009;56(1):182-92. doi: 10.1109/TUFFC.2009.1018.

International Search Report and Written Opinion dated Nov. 5, 2019 in connection with International Application No. PCT/US2019/030482.

Taiwan Preliminary Examination Report dated Sep. 14, 2022 issued in corresponding Taiwan Appln. No. 108115240.

* cited by examiner

ULTRASOUND DEVICES

CROSS-REFERENCE TO RELATED APPLICATION

This application claims the benefit under 35 U.S.C. § 119(e) of U.S. Provisional Patent Application Ser. No. 62/666,643, entitled "ULTRASOUND DEVICES," filed on May 3, 2018, which is hereby incorporated herein by reference in its entirety.

FIELD

Generally, the aspects of the technology described herein relate to ultrasound devices.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

BRIEF SUMMARY

Some embodiments relate to an ultrasound device comprising an ultrasonic transducer disposed on a complementary metal-oxide-semiconductor (CMOS) substrate and having an electrode wherein a central portion of the electrode is absent.

Some embodiments relate to an ultrasound device comprising a membrane, a first bond pad disposed with a trench that electrically isolates the first bond pad from the membrane, and a second bond pad that is not electrically isolated from the membrane.

Some embodiments relate to an ultrasound device comprising an ultrasonic transducer disposed on a complementary metal-oxide-semiconductor (CMOS) substrate and having an electrode wherein a central portion of the electrode is absent.

In some embodiments, the electrode is a first electrode, and wherein the ultrasonic transducer further comprises a membrane and a cavity disposed between the membrane and the first electrode.

In some embodiments, the ultrasound device further comprises a second electrode disposed in the central portion of the first electrode.

In some embodiments, the second electrode is electrically coupled to ground.

In some embodiments, the ultrasound device further comprises a metal extending beneath the cavity and disposed a distance away from the first electrode.

In some embodiments, the metal is electrically coupled to ground.

In some embodiments, the first electrode is circular, and the first electrode comprises slots extending along a radial direction of the first electrode.

In some embodiments, the ultrasound device further comprises a redistribution layer disposed beneath the first electrode, wherein the redistribution layer is electrically coupled to ground.

In some embodiments, a bottom surface of the membrane facing the cavity comprises aluminum oxide.

In some embodiments, a bottom surface of the membrane facing the cavity comprises hafnium oxide.

In some embodiments, the first electrode comprises titanium.

In some embodiments, the first electrode comprises tungsten.

In some embodiments, wherein the first electrode is formed with a damascene process.

In some embodiments, the first electrode is formed with a dual damascene process.

In some embodiments, the first electrode comprises a sea of vias.

Some embodiments relate to an ultrasound device comprising a membrane;
a first bond pad disposed with a trench that electrically isolates the first bond pad from the membrane; and a second bond pad that is not electrically isolated from the membrane.

In some embodiments, the ultrasound device further comprises a complementary metal-oxide-semiconductor (CMOS) chip disposed beneath the membrane; and a first metal extending from the second bond pad along a top surface of the ultrasound device to the membrane. The first metal is not electrically coupled to the CMOS chip.

In some embodiments, the ultrasound device further comprises second metal disposed between the first metal and the CMOS chip.

In some embodiments, the ultrasound device further comprises a first electrode and a cavity disposed between the membrane and the first electrode, wherein a central portion of the first electrode is absent.

In some embodiments, the ultrasound device further comprises a second electrode disposed in the central portion of the first electrode.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Aspects of the present application relate to ultrasound devices having membranes for producing ultrasonic signals, and in which center portions of the sensing electrodes 106 are absent. A sensing electrode is an electrode positioned near a membrane to cause and/or detect vibrations of the membrane.

Applicant has appreciated that, in some ultrasound devices, the electric field existing between a membrane and a sensing electrode may be sufficient to cause a portion of the membrane to contact a portion the sensing electrode. The portion of the membrane that contacts the portion of the sensing electrode may be a central portion of the membrane, and the portion of the sensing electrode on which the portion of the membrane collapses may be a central portion of the sensing electrode. When such a contact occurs, the central portion of the membrane may not contribute to production of ultrasonic signals. Therefore, any signal applied to the central portion of the sensing electrode does not contribute to production of ultrasonic signals. A parasitic capacitance may nonetheless exist between the center portion of the sensing electrode and the center portion of the membrane, thus negatively affecting the sensitivity with which the ultrasound device detects ultrasound signals.

According to some aspects of the present application, the aforementioned problem may be addressed by providing ultrasound devices in which the center portion of a sensing electrode is absent. For example, a sensing electrode 106 may be shaped as a ring with a circular portion of the center being absent. Ultrasound devices in which the center portion of a sensing electrode is absent may exhibit a reduced parasitic capacitance, without substantially affecting the production of ultrasonic signals. This, in turn, can result in an increase in the sensitivity of the ultrasound device.

According to other aspects of the present application, ultrasound devices of the types described herein may be electrically interfaced with other electronic devices using wire bonding. Thus, some ultrasound devices include bond pads on which wires are bonded. A first bond pad may serve as the point of access to electronic circuitry designed to control the operations of the ultrasound device. A second bond pad may serve as the point of access to a membrane. To ensure proper operations, the first bond pad should be electrically isolated from the membrane.

Applicant has appreciated, however, that conductors are used for electrically connecting the first bond pad to the electronic circuitry, and that the presence of such conductors could inadvertently short any voltage applied at the first bond pad to the membrane. To limit the risk that the membrane be shorted to the first bond pad, in some embodiments, the ultrasound device includes a trench formed between the first bond pad and the membrane to ensure electrical isolation. In some embodiments, the trench may surround the first bond pad.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 1:
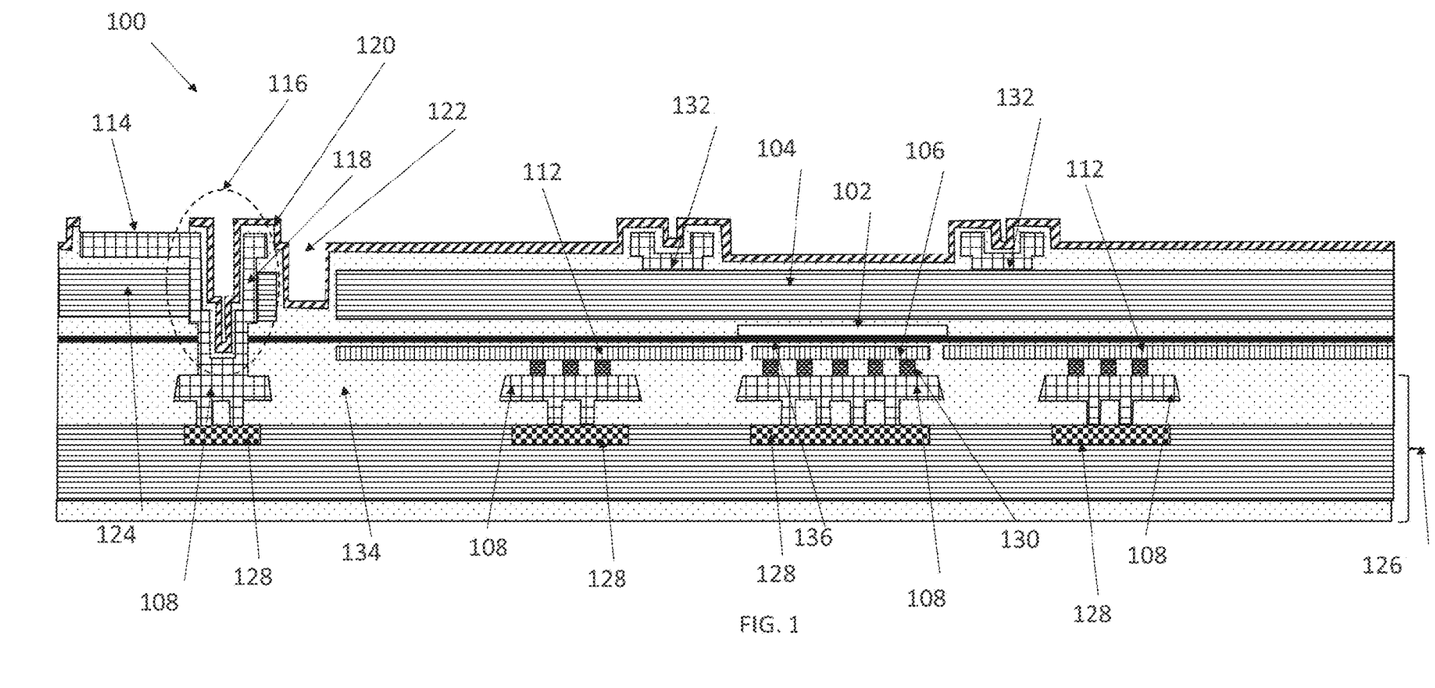
FIG. 1 illustrates an example cross-section of an ultrasound device 100 in accordance with certain embodiments described herein.

FIG. 1 illustrates an example cross-section of an ultrasound device 100 in accordance with certain embodiments described herein. The ultrasound device includes a cavity 102, a membrane 104, and a sensing electrode 106. When an electrical signal is applied to the sensing electrode 106 and a static bias is applied to the membrane 104, the membrane 104 may vibrate within the cavity 102 and produce ultrasonic signals. The cavity 102, the membrane 104, and the sensing electrode 106 may be considered a capacitive micromachined ultrasonic transducer (CMUT). Electrical contact to the membrane 104 may be made through contacts 132, as will be described further below, in order to supply a bias voltage to the membrane 104. The ultrasound device 100 includes oxide 134 that may insulate various portions of the ultrasound device 100, or be deposited for specific purposes during fabrication of the ultrasound device 100. While the oxide 134 is shown as one continuous portion, the oxide 134 may be formed during different steps in different portions of the ultrasound device 100 using different processes. For example, the cavity 102 may be etched in oxide formed using high-density plasma (HDP) chemical vapor deposition (CVD), while other oxide in the ultrasound device 100 may be thermal oxide. The top surface of the ultrasound device 100 may be passivated with passivation 120 (e.g., silicon oxide and silicon nitride).

The ultrasound device 100 includes a complementary metal-oxide-semiconductor (CMOS) chip 126. The CMOS chip 126 may include silicon (in which semiconductor devices may be formed) and oxide on the bottom surface as passivation. The CMOS chip 126 may include integrated circuitry (not shown in FIG. 1) for controlling operation of the ultrasound device 100. For example, the integrated circuitry may provide electrical signals to the sensing electrode 106 and receive and process electrical signals from the sensing electrode 106. The CMOS chip 126 includes metal 128 that may serve as interconnect for routing electricity in the CMOS chip 126. The metal 128 may include two or more vertically stacked layers of metal wiring, with vias connecting the different layers. The CMOS chip 126 further includes a redistribution layer (RDL) 108. The RDL 108 may include mainly aluminum (with a small portion of copper and/or silicon), or copper. The RDL 108 may be used to redistribute signals in the CMOS chip 126. For example, in FIG. 1, the RDL 108 may electrically contact the sensing electrode 106 through vias 130, and route signals to the sensing electrode 106 from the metal 128 of the CMOS chip 126. The RDL 108 may include two or more vertically stacked layers connected with vias. In the ultrasound device 100, the RDL 108 may also be used to shield the sensing electrode 106, as will be described further below.

In some embodiments, the membrane 104 may include silicon and a layer of oxide on its bottom surface. In some embodiments, the oxide may be thermal oxide (e.g., formed with wet oxidation, dry oxidation, or a dry-wet-dry cycle) while in other embodiments the oxide on the bottom surface of the membrane may be aluminum oxide or hafnium oxide (e.g., formed with atomic layer deposition (ALD)). In some embodiments, the sensing electrode 106 may include titanium, titanium nitride, and/or tungsten. In embodiments in which the sensing electrode 106 includes tungsten, the vias 130 may also include tungsten, and the sensing electrode 106 and the vias 130 may be formed with a dual damascene process. In some embodiments, the sensing electrode 106 may be formed from a sea (a large plurality) of tungsten vias formed with a single damascene process. In some embodiments, the vias 130 and/or the sensing electrode 106 can include copper.

Figure 2:
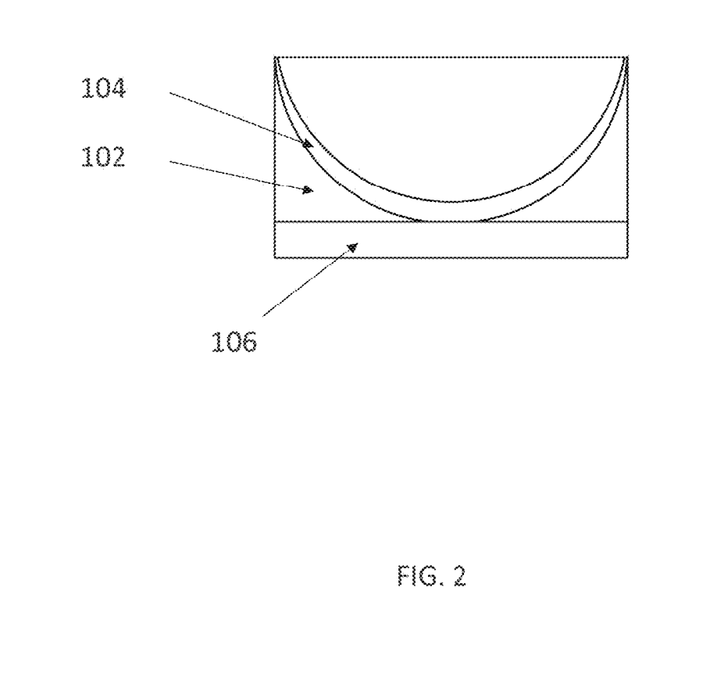
FIG. 2 illustrates an example side view of a cavity, a membrane, and a sensing electrode in accordance with certain embodiments described herein.

FIG. 2 illustrates an example side view of the cavity 102, the membrane 104, and the sensing electrode 106 in accordance with certain embodiments described herein. FIG. 2 illustrates the membrane 104 in a mode in which the electric field between the membrane 104 and the sensing electrode 106 is sufficient to cause a portion of the membrane 104 to contact a portion the sensing electrode 106. This may be considered a collapse mode, and the voltage between the membrane 104 and the sensing electrode 106 required to cause the membrane 104 to enter collapse mode may be considered the collapse voltage. The portion of the membrane 104 that contacts the portion of the sensing electrode 106 in collapse mode may be a central portion of the membrane 104, and the portion of the sensing electrode 106 on which the portion of the membrane 104 collapses may be a central portion of the sensing electrode 106. In collapse mode, the central portion of the membrane 104 does not vibrate in response to the electrical signal applied to the sensing electrode 106. Therefore, in collapse mode, the central portion of the membrane 104 does not contribute to production of ultrasonic signals, and any signal applied to the central portion of the sensing electrode 106 does not contribute to production of ultrasonic signals. However, a parasitic capacitance may exist between the sensing electrode 106 and the membrane 104.

With repeated collapsing of the membrane 104 onto the sensing electrode 106 during the lifetime of the ultrasound device 100, charge may accumulate on the membrane 104, the bottom of which is an insulator (e.g., oxide). This charging of the membrane 104 may counteract the voltage applied between the membrane 104 and the sensing electrode 106. More charging may occur on the central portion of the membrane 104 compared with other portions of the membrane 104, as the central portion of the membrane 104 may contact the sensing electrode 106 during collapse most often.

Figure 3:
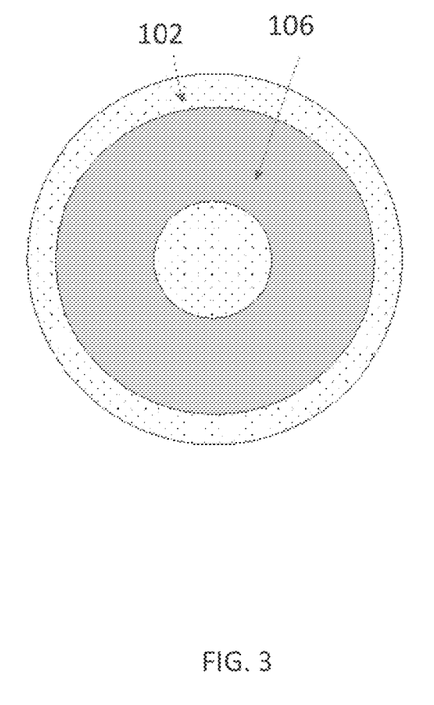
FIG. 3 illustrates an example top view of a cavity and sensing electrode in accordance with certain embodiments described herein.

FIG. 3 illustrates an example top view of the cavity 102 and the sensing electrode 106 in accordance with certain embodiments described herein. The sensing electrode 106 may be considered ring-shaped in that a circular portion of the center portion of the sensing electrode 106 is absent. As described above, in collapse mode, the central portion of the sensing electrode 106 may not contribute to production of ultrasonic signals. However, the central portion of the sensing electrode 106 may contribute to parasitic capacitance. In a ring-shaped sensing electrode 106, the removal of the central portion of the sensing electrode 106 may reduce the parasitic capacitance without substantially affecting the production of ultrasonic signals by the CMUT in collapse mode. This, in turn, can result in an increase in the signal-to-noise ratio (SNR) of the ultrasonic signals. In some embodiments, the outer diameter of the sensing electrode 106 may be approximately 55-115 microns, approximately 70-100 microns, or approximately 85 microns. In some embodiments, the inner diameter of the sensing electrode 106 may be approximately 40-50 microns.

With the central portion of the sensing electrode 106 absent, a larger collapse voltage may be needed for the CMUT to enter collapse mode than if the central portion of the sensing electrode 106 were not absent. A larger collapse voltage may result in a larger electric field existing between the membrane 104 and the sensing electrode 106, which may in turn result in greater sensitivity of the CMUT to received ultrasonic signals.

Additionally, the central portion of the sensing electrode 106 may be the portion of the sensing electrode 106 that causes the most charging on the membrane 104. Because the central portion of the sensing electrode 106 is absent, this charging may be reduced. The outer regions of the membrane 104 may not be charged as much as the central portion of the membrane 104 would if the central portion of the sensing electrode 106 were present, as the outer regions of the membrane 104 may not contact the ring-shaped sensing electrode 106 as often during collapse.

Figure 4:
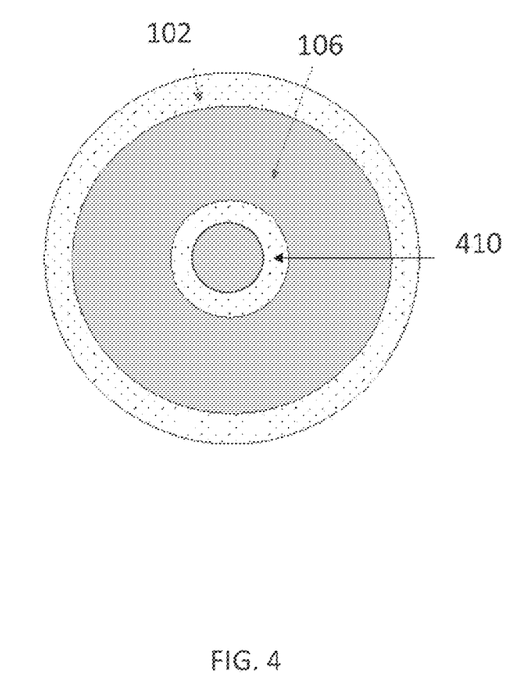
FIG. 4 illustrates an example top view of a cavity and sensing electrode with an additional electrode included in the empty central portion of the sensing electrode in accordance with certain embodiments described herein.

FIG. 4 illustrates an example top view of the cavity 102 and the sensing electrode 106 with an additional electrode 410 included in the empty central portion of the sensing electrode 106 in accordance with certain embodiments described herein. The sensing electrode 106 may be similar to the sensing electrode 106 of FIG. 3. The electrode 410 may be coupled to ground. The electrode 410 may contribute to a bypass capacitance between the membrane 104 and ground. Noise from the metal 128 (e.g., metal 128 carrying voltage for supplying power) may couple to metal 112. The noise may be reduced, at least in part, by the presence of the RDL 108. The bypass capacitance between the membrane 104 and ground may further reduce the noise on metal 112 coupled from metal 128. In some embodiments, the electrode 410 may contribute to a lower collapse voltage compared with the collapse voltage of the embodiment shown in FIG. 3. This may be because, in some embodiments, the ground electrode 410 may contribute to attracting the membrane 104 towards the bottom of the cavity 102. Higher electric fields in the cavity 102 may contribute to greater charging of the membrane 104 (e.g., the oxide at the bottom surface of the membrane 104) due to repeated collapsing, and therefore it may be helpful to reduce the voltage required to achieve collapse in order to reduce charging.

Figure 5:
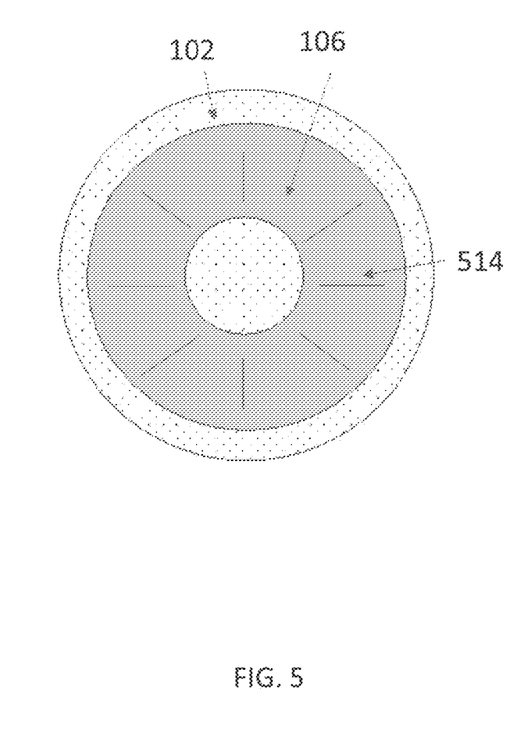
FIG. 5 illustrates an example top view of a cavity and sensing electrode in accordance with certain embodiments described herein.

FIG. 5 illustrates an example top view of the cavity 102 and the sensing electrode 106 in accordance with certain embodiments described herein. The sensing electrode 106 includes slots 514 (i.e., empty space). The slots 514 may be required by design rules for manufacturing the ultrasound device 100. The slots 514 extend along the radial direction of the sensing electrode 106. As the membrane 104 contacts the sensing electrode 106 during collapse, the membrane 104 may first contact a small portion of the center of the sensing electrode 106, then a larger portion of the center of the sensing electrode 106, etc. In other words, the membrane 104 may progressively contact the sensing electrode 106 in a radial direction. Because the slots 514 extend along the radial direction of the sensing electrode 106, a small change in contact of the membrane 104 with the sensing electrode 106 may correspond to a small change in contact of the membrane 104 with one or more of the slots 514. If the slots 514 did not extend along the radial direction, it could be possible for a small change in contact of the membrane 104 with the sensing electrode 106 to correspond to a large change in contact of the membrane 104 with one or more of the slots 514, which could cause a disturbance in the performance of the CMUT. Arranging the slots along the radial direction of the sensing electrode 106 may reduce this disturbance. It should be appreciated that slots 514 may be used in either of the embodiments shown in FIGS. 3 and 4.

Referring back to FIG. 1, the ultrasound device 100 includes an oxide layer 136 at the bottom of the cavity 102. The oxide layer 136 may include, for example, aluminum oxide or hafnium oxide. The oxide layer 136 may be formed by atomic layer deposition (ALD). Because the membrane 104 includes oxide on its bottom surface, during collapse, the oxide of the membrane 104 may contact oxide at the bottom of the cavity 102. Because an insulator contacts another insulator, charging of the membrane 104 may be reduced. In some embodiments, the oxide on the bottom surface of the membrane may be thermal oxide (e.g., formed with wet oxidation, dry oxidation, or a dry-wet-dry cycle) while in other embodiments the oxide on the bottom surface of the membrane may be aluminum oxide or hafnium oxide (e.g., formed with ALD).

Figure 6:
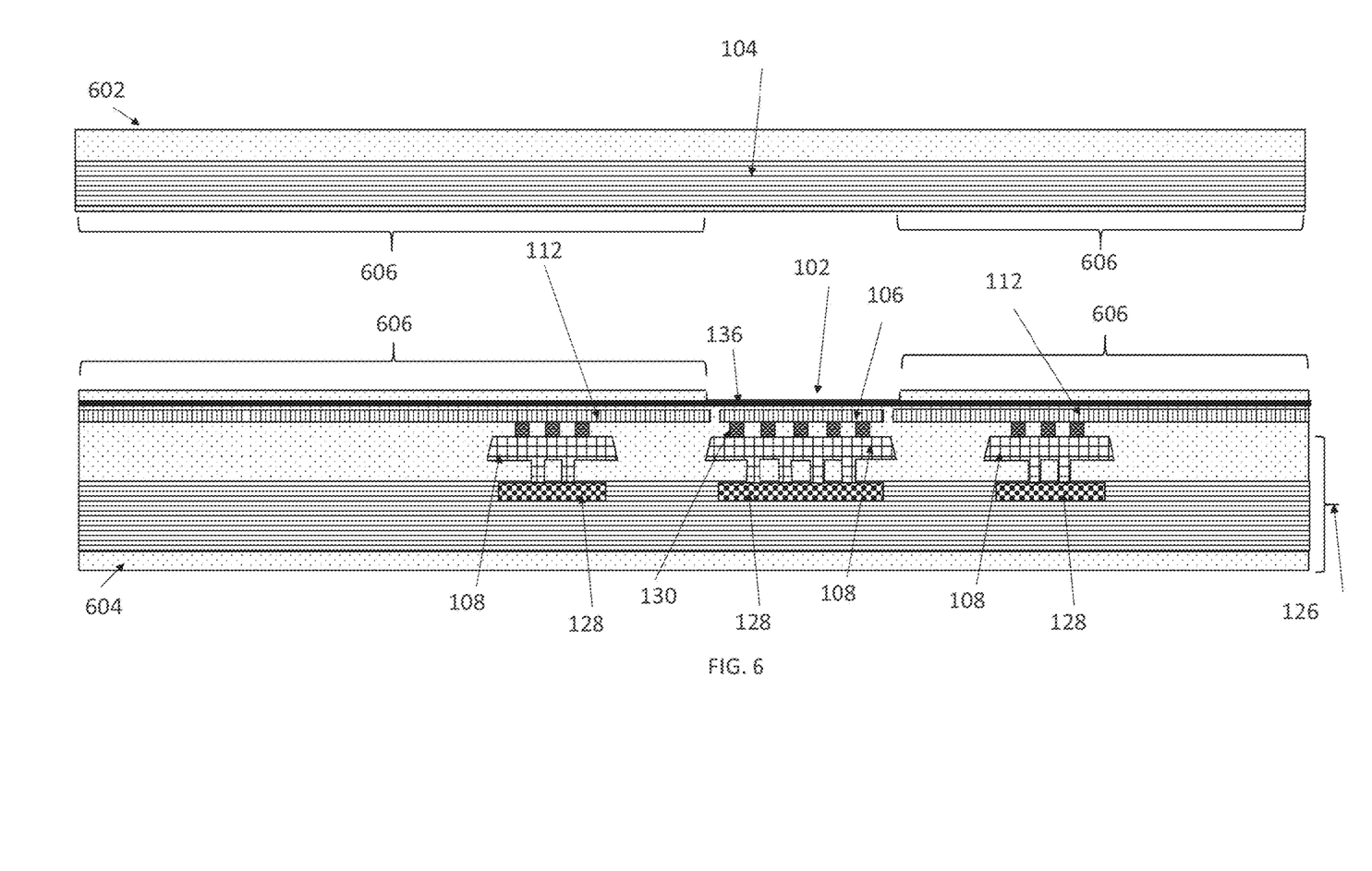
FIG. 6 illustrates how in some embodiments the ultrasound device 100 is formed by bonding two substrates together.

The ultrasound device 100 includes metal 112. The metal 112 extends below the cavity 102, and may include the same material as the sensing electrode 106. As shown in FIG. 6, in some embodiments the ultrasound device 100 is formed by bonding two substrates together. The top substrate 602 includes the membrane 104 and the bottom substrate 604 includes the cavity 102, the sensing electrode 106, and the metal 112. Bonding occurs at bonding interfaces 606 between the top substrate 602 and the bottom substrate 604. As can be seen, bonding does not occur at the cavity 102. The metal 112 extends along the length of the bonding interface 606 in the bottom substrate 604. This may contribute to the structures below the bonding interface 606 in the bottom substrate 604 being substantially homogenous along the length of the bonding interface 606, which may in turn contribute to the top surface of the bottom substrate 604 being substantially homogenous along the bonding interface 606. This homogeneity may help to ensure homogeneity of the bonding between the two substrates. (While the RDL 108, the metal 128, and other structures further below the bonding interface 606 may not be homogenous along the bonding interface 606, these structures may contribute less to homogeneity of the top surface of the bottom substrate 604 than structures closer to the top of the bottom substrate 604). Gaps between the metal 112 and the sensing electrode 106, which could potentially cause inhomogeneity of the top surface of the bottom substrate 604, are below the cavity 102 where no bonding occurs. The metal 112 may be connected to ground in the CMOS chip 126 through the vias 130, the RDL 108, and the metal 128. The metal 112 may further serve as bypass capacitance between top membrane 104 and ground. In some embodiments, the gap between the sensing electrode 106 and the metal 112 may be approximately 4-6 microns, such as approximately 5 microns. In some embodiments, the metal 112 may extend approximately 6-10 microns, such as approximately 8 microns, beneath the cavity 102.

Referring back to FIG. 1, the bond pad 114 may be used for electrically coupling (e.g., using wire bonding) the ultrasound device 100 to a package (e.g., a package for mounting on a printed circuit board). Voltage at the bond pad 114 may be transmitted to the RDL 108 through the via 116. The via 116 includes metal 118 connecting the bond pad 114 to the RDL 108 and the passivation 120 over the metal 118. The metal 118 could contact the membrane 104 as the metal 118 passes from the bond pad 114 to the RDL 108. The presence of metal 118 could short any voltage applied at the bond pad 114 to the membrane 104. This may not be desirable if the voltage applied at the bond pad 114 is not intended to be applied to the membrane 104 (e.g., if the voltage is analog or digital voltage for powering or controlling certain circuits in the CMOS chip 126). To limit the risk that membrane 104 be shorted to bond pad 114, the ultrasound device 100 includes a trench 122 that extends around the bond pad 114 (or otherwise between bond pad 114 and membrane 104) that electrically isolates the membrane 104 from the metal 118. (The full extension of the trench 122 around the bond pad 114 is not visible in FIG. 1.) Due to the electrical isolation of the membrane 104 from the metal 118 of the via 116, a voltage applied at the bond pad 114 may not short to the membrane 104. (The metal 118 does contact a portion 124 that is formed from the same layer as the membrane 104, but this portion 124 does not overlay a cavity 102 and therefore any shorting of the bond pad 114 to the portion 124 may not substantially affect ultrasonic performance of the ultrasound device 100.)

Figure 7:
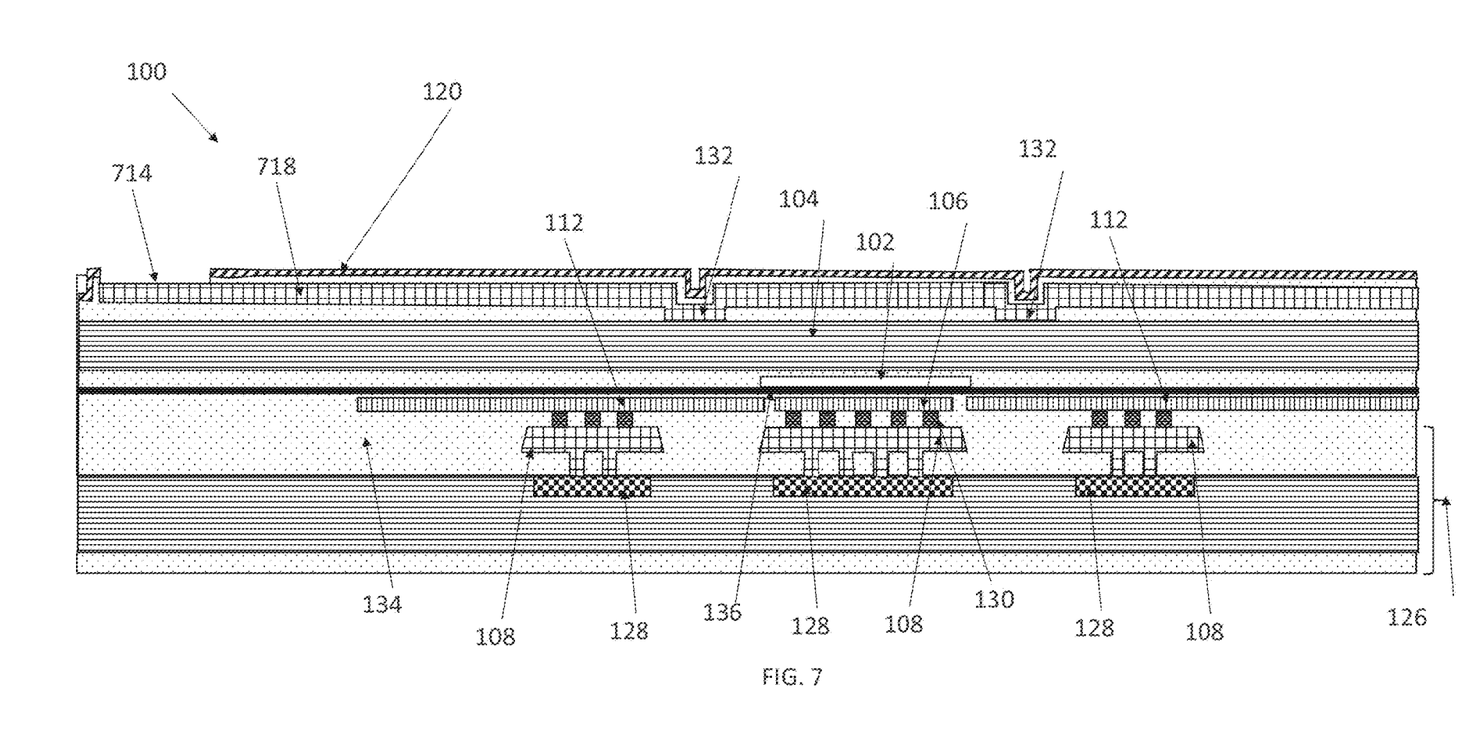
FIG. 7 illustrates an example cross-section of an ultrasound device in accordance with certain embodiments described herein.

FIG. 7 illustrates an example cross-section of an ultrasound device 100 in accordance with certain embodiments described herein. The cross-section of FIG. 7 may be along a different plane of the ultrasound device 100 than the cross-section of FIG. 1. FIG. 7 shows a bond pad 714 that may be used for electrically coupling (e.g., using wire bonding) the ultrasound device 100 to a package (e.g., a package for mounting on a printed circuit board). In particular, the bond pad 714 is electrically connected to the membrane 104. Voltage for biasing the membrane 104 may be applied at the bond pad 714. A trench is therefore not needed around the bond pad 714 to isolate the bond pad 714 from the membrane 104, as opposed to the trench 122 which may be needed to isolate the bond pad 114 (at which other voltages that should not short to the membrane 104 may be applied) from the membrane 104. Furthermore, as seen in FIG. 7, a metal 718 connects the bond pad 714 to the membrane 104, with the metal 718 extending across the top of the ultrasound device 100 to the electrical contact 132, as opposed to the metal 118, which extended down to the RDL 108. It may be helpful for the metal 718 not to extend down to the RDL 108 of the CMOS chip 126 because the voltage applied to the membrane 104 may be a high voltage (e.g., 80V-100V) and certain materials of the CMOS chip 126 may not perform properly when exposed to such high voltages. The metal 118 avoids this high voltage from extending into the CMOS chip 126.

Figure 8:
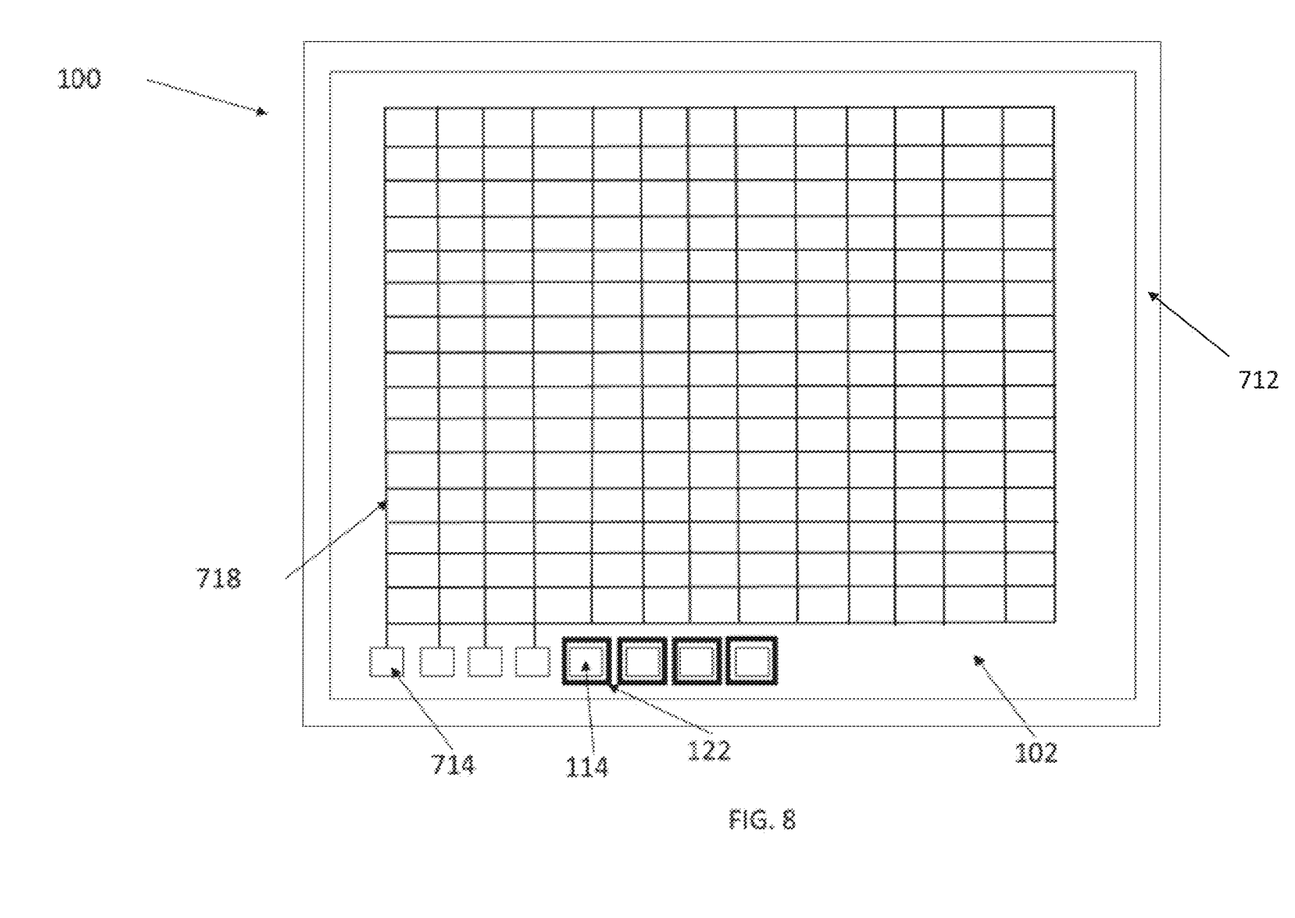
FIG. 8 illustrates an example top view of an ultrasound device in accordance with certain embodiments described herein.

FIG. 8 illustrates an example top view of the ultrasound device 100 in accordance with certain embodiments described herein. FIG. 8 shows the membrane 104, which extends across the top surface of the ultrasound device 100, the bond pads 714 which provide bias voltage to the membrane 104, the metal 718, the bond pads 114 which provide voltages that should not short to the membrane 104 (e.g., analog or digital voltages for powering or controlling certain circuits in the CMOS chip 126), and the trenches 122. The metal 718 extends from the bond pads 714 and forms a network that distributes the bias voltage from the bond pads 714 to the membrane 104. The trenches 122 isolate the bond pads 114 from the membrane 104. It should be appreciated that the passivation 120 and other structures may overlay the membrane 104 but are not shown in FIG. 8. In some embodiments, ultrasound device 100 includes a trench 712 around the periphery of a die. The trench 712 may separate contiguous dies from one another, and may facilitate dicing. For example, trench 712 may provide a channel in which a die-saw blade is inserted and actuated during dicing. Use of trench 712 may reduce the likelihood that the dies are damaged during dicing.

Figure 9:
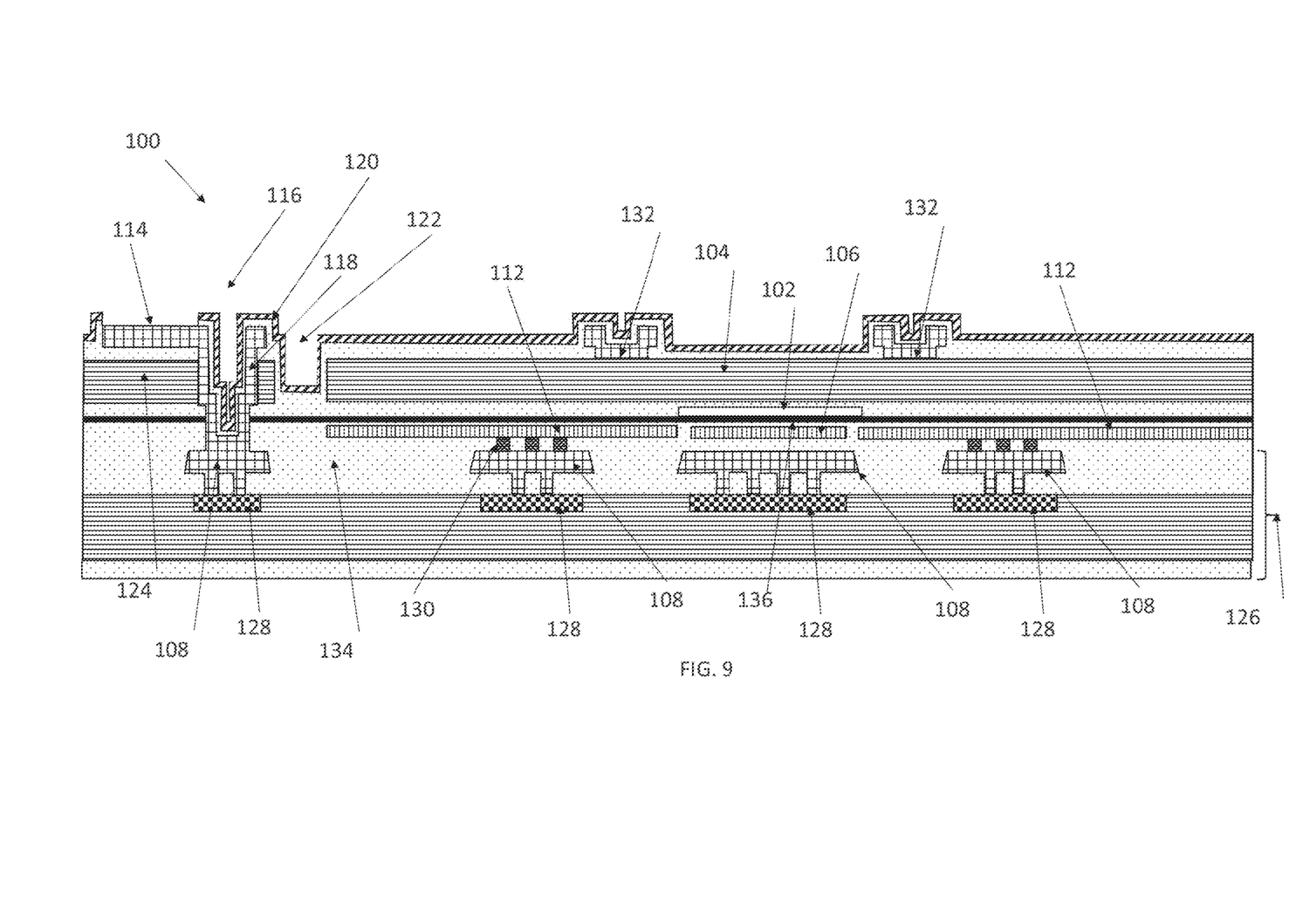
FIG. 9 illustrates an example cross-section of an ultrasound device in accordance with certain embodiments described herein.

FIG. 9 illustrates an example cross-section of an ultrasound device 100 in accordance with certain embodiments described herein. The cross-section of FIG. 9 may be along a different plane of the ultrasound device 100 than the cross-section of FIG. 1. In FIG. 9, the RDL 108 below the sensing electrode 106 is not electrically coupled to the sensing electrode 106. The RDL 108 may be electrically coupled to ground in the CMOS chip 126 through the metal 128. There may be power lines within the metal 128 that run under the sensing electrode 106. Noise on these power lines may couple to the sensing electrode 106. The RDL 108 below the sensing electrode 106 that is electrically coupled to ground may help to shield the sensing electrode 106 from this noise. In some embodiments, one layer of the RDL 108 may be used to electrically couple the sensing electrode 106 to the CMOS chip 126 while another layer of the RDL 108 may be electrically coupled to ground in the CMOS chip 126 and be used to shield the sensing electrode 106.

In some embodiments, the vias 130 may be planarized (e.g., using chemical mechanical planarization (CMP)) prior for forming the sensing electrode 106 on the vias 130. The sensing electrode 106 may then be planarized (e.g., using CMP). The oxide in which the cavity 102 is formed may then be deposited (e.g., using HDP-CVD) on the planarized sensing electrode 106. By virtue of the planarization of the sensing electrode 106 and vias 130, the oxide in which the cavity 102 is formed may not require planarization after deposition. This may be helpful, because the thickness of the deposited oxide in which the cavity 102 is formed may dictate the depth of the cavity 102, and it may be desirable to tightly control this depth. Planarization of the oxide could reduce the depth of the cavity 102 from the desired depth and/or loosen control over the depth of the cavity 102. Avoiding planarization of the oxide may help to maintain control over the depth of the cavity 102. In some embodiments, the vias 130 may be formed without planarization, the sensing electrode 106 may be formed on the vias 130, and the sensing electrode 106 may then be planarized. Planarization may ensure that the roughness of the oxide in which the cavity 102 is formed is less than 5 angstroms. It should be appreciated that the same steps used for forming the sensing electrode 106 may be used for forming the metal 112.

Aspects of the present application may provide one or more benefits, some of which have been previously described. Now described is a non-limiting example of such benefits. It should be appreciated that not all aspects and embodiments necessarily provide all of the benefits now described. Further, it should be appreciated that aspects of the present application may provide additional benefits to the one now described.

Aspects of the present application provide ultrasound devices with sensing electrodes shaped to reduce undesired parasitic capacitances without substantially affecting the production of ultrasonic signals. In this way, the signal-to-noise ratio associate with the detection signal is increased, and so is the ultrasound device's ability to form images.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having,"

"containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device comprising:
   a membrane proximate a surface of the ultrasound device;
   a substrate distal from the surface;
   an ultrasonic transducer comprising a cavity disposed between the membrane and the substrate;
   a first bond pad configured for wire bonding and disposed at the surface of the ultrasound device, the first bond pad being electrically isolated from the membrane by a trench formed through the membrane;
   a second bond pad configured for wire bonding and disposed at the surface of the ultrasound device and electrically coupled to the membrane; and
   a first electrode having an inner circumference and an outer circumference and radial slots integrated within the first electrode, each of the radial slots having a first end terminating proximate to the inner circumference and proceeding radially to a second end terminating proximate to the outer circumference of the first electrode, wherein the cavity is disposed between the membrane and the first electrode.

2. The ultrasound device of claim 1, wherein the substrate comprises a complementary metal-oxide-semiconductor (CMOS) chip, and further comprising:
   a first metal extending from the second bond pad along the surface of the ultrasound device to the membrane;
   wherein the first metal is electrically isolated from the CMOS chip.

3. The ultrasound device of claim 2, further comprising a second metal disposed between the first metal and the CMOS chip.

4. The ultrasound device of claim 1, wherein a central portion of the first electrode is absent.

5. The ultrasound device of claim 4, further comprising a second electrode disposed in the central portion of the first electrode.

* * * * *